(12) United States Patent
Streeter

(10) Patent No.: US 7,070,618 B2
(45) Date of Patent: Jul. 4, 2006

(54) MITRAL SHIELD

(75) Inventor: Richard B. Streeter, Winchester, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

(21) Appl. No.: 10/004,068

(22) Filed: Oct. 25, 2001

(65) Prior Publication Data

US 2002/0065554 A1    May 30, 2002

Related U.S. Application Data

(60) Provisional application No. 60/243,234, filed on Oct. 25, 2000.

(51) Int. Cl.
*A61F 2/24*    (2006.01)

(52) U.S. Cl. .................... 623/2.36; 623/2.2; 623/2.33

(58) Field of Classification Search ...... 623/2.11–2.13, 623/2.1, 2.2, 2.27–2.33, 2.36–2.41; A61F 2/24
See application file for complete search history.

(56) References Cited

U.S. PATENT DOCUMENTS

| | | | | |
|---|---|---|---|---|
| 4,042,979 A | * | 8/1977 | Angell | 623/2.37 |
| 4,489,446 A | * | 12/1984 | Reed | 623/2.36 |
| 4,917,698 A | * | 4/1990 | Carpentier et al. | 623/2.36 |
| 5,061,277 A | * | 10/1991 | Carpentier et al. | 623/2.36 |
| 5,201,880 A | * | 4/1993 | Wright et al. | 623/2.36 |
| 5,360,444 A | * | 11/1994 | Kusuhara | 623/2.36 |
| 5,709,695 A | * | 1/1998 | Northrup, III | 623/2.36 |
| 6,406,420 B1 | * | 6/2002 | McCarthy et al. | 600/16 |
| 6,419,695 B1 | * | 7/2002 | Gabbay | 623/2.36 |
| 6,524,338 B1 | * | 2/2003 | Gundry | 623/2.11 |
| 6,702,826 B1 | * | 3/2004 | Liddicoat et al. | 606/151 |
| 2003/0120340 A1 | * | 6/2003 | Liska et al. | 623/2.1 |

FOREIGN PATENT DOCUMENTS

| | | | |
|---|---|---|---|
| DE | 296 18 925 U1 | * | 1/1997 |
| JP | 11-299814 | * | 11/1999 |
| WO | WO 98/32401 A1 | * | 7/1998 |
| WO | WO 03/053289 A1 | * | 7/2003 |

* cited by examiner

*Primary Examiner*—David H. Willse
*Assistant Examiner*—Javier G. Blanco
(74) *Attorney, Agent, or Firm*—Pandiscio & Pandiscio

(57) ABSTRACT

A valve shield comprising a shaped sheet of material adapted to be affixed to the annulus of a valve and adapted to extend over at least a portion of at least one leaflet of the valve so as to assist or replace the closing function of that valve leaflet.

9 Claims, 4 Drawing Sheets

MITRAL SHIELD

REFERENCE TO PENDING PRIOR PATENT APPLICATION

This patent application claims benefit of pending prior U.S. Provisional Patent Application Ser. No. 60/243,234, filed Oct. 25, 2000 by Richard B. Streeter for MITRAL SHIELD, which patent application is hereby incorporated herein by reference.

FIELD OF THE INVENTION

This invention relates to surgical apparatus and methods in general, and more particularly to apparatus and methods for addressing mitral regurgitation.

BACKGROUND OF THE INVENTION

Mitral valve repair is the procedure of choice to correct mitral regurgitation of all etiologies. With the use of current surgical techniques, between 70% and 95% of regurgitant mitral valves can be repaired. The advantages of mitral valve repair over mitral valve replacement are well documented. These include better preservation of cardiac function and reduced risk of anticoagulant-related hemorrhage, thromboembolism and endocarditis.

Degenerative mitral valve disease most commonly affects the chordae of the posterior leaflet, causing posterior leaflet prolapse. Traditional repair techniques for such lesions include leaflet resection and annular plication.

SUMMARY OF THE INVENTION

One object of the present invention is to provide novel apparatus and method for the repair of heart valves so as to increase their efficiency.

Another object of the present invention is to provide novel apparatus and method for the repair of mitral valves so as to reduce mitral regurgitation.

And another object of the present invention to provide novel apparatus and method to correct mitral valve regurgitation caused by mitral valve leaflet prolapse or posterior annulus dilation.

These and other objects are addressed by the provision and use of the present invention, which comprises a shaped sheet of material affixed to the annulus of the valve and extending over at least one leaflet of the valve so as to assist or replace the closing function of that valve leaflet. The device may be used for mitral valve repair or for other valve repair, on a beating heart or on an arrested heart.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
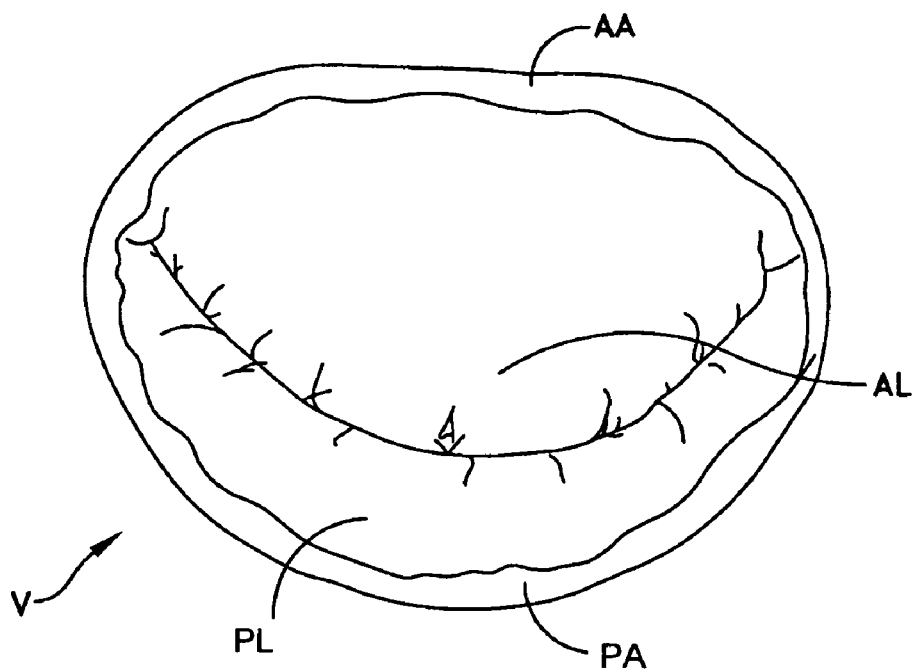
FIG. 1 is a schematic view showing a normal mitral valve in its closed position.

Looking first at FIG. 1, there is shown a normal mitral valve V. Mitral valve V is shown in its closed position, with its posterior leaflet PL and its anterior leaflet AL properly engaging one another. Also shown is the valve's posterior annulus PA and its anterior annulus AA.

Figure 2:
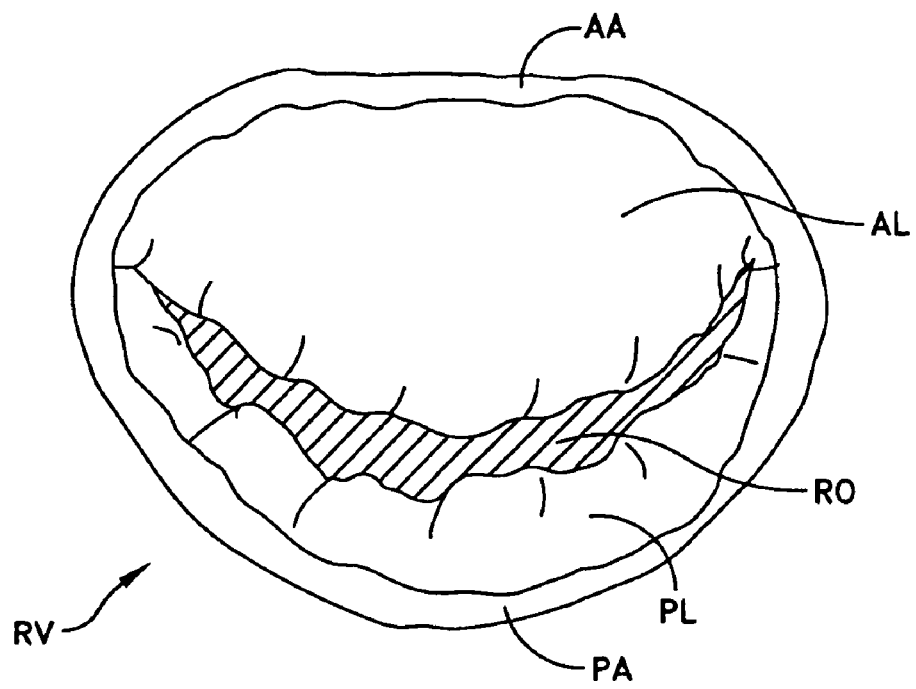
FIG. 2 is a schematic view showing a regurgitant mitral valve in its closed position, with its posterior leaflet in a prolapsed condition.

Looking next at FIG. 2, there is shown a regurgitant mitral valve RV. Regurgitant mitral valve RV is shown in its closed position, with posterior leaflet PL in a prolapsed condition and failing to properly engage anterior leaflet AL, thus leaving a regurgitant orifice RO therebetween.

Figure 3:
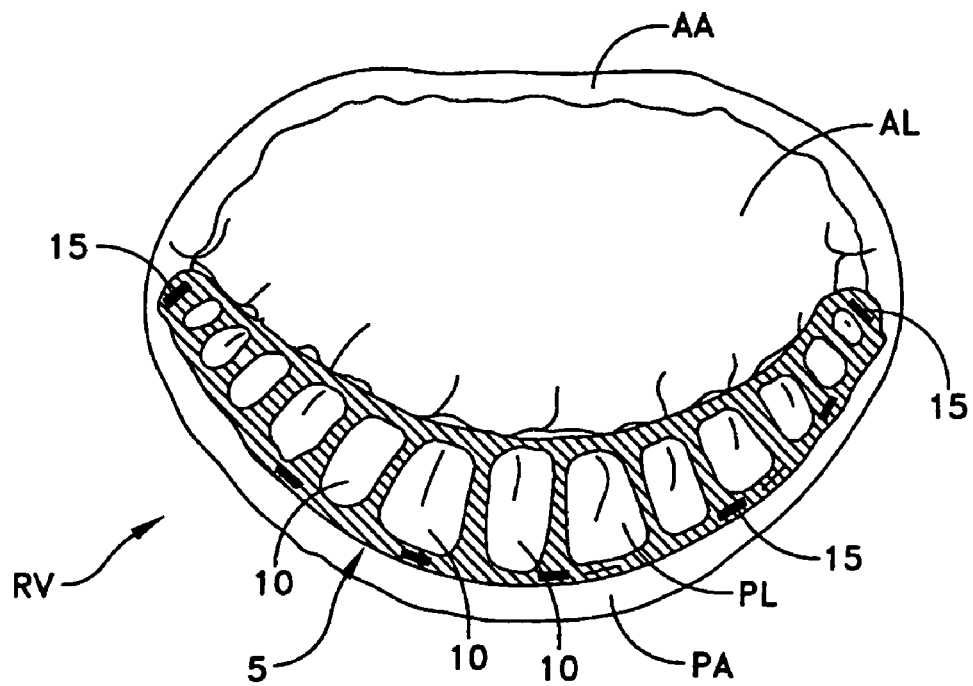
FIG. 3 is a schematic view showing a mitral shield affixed to the periphery of the regurgitant mitral valve of FIG. 2 so as to prevent prolapse of the posterior leaflet and thereby ameliorate mitral regurgitation.

Looking next at FIG. 3, a mitral shield 5 is shown affixed to the posterior annulus PA of the valve RV so as to prevent prolapse of the posterior leaflet PL and thereby ameliorate mitral regurgitation.

More particularly, mitral shield 5 comprises a shaped sheet of material which is sized to the circumference of the mitral annulus. This sheet may be uniform in thickness or specifically shaped to match the surface of the mitral valve. When affixed to the valve annulus, the sheet will project over a portion of the orifice of the mitral valve. In most cases, the sheet will be oriented over the posterior leaflet PL, such as is shown in FIG. 3, thereby providing an area of contact for the anterior mitral leaflet AL and reducing or eliminating regurgitation due to leaflet prolapse by the posterior leaflet PL.

Figure 4:
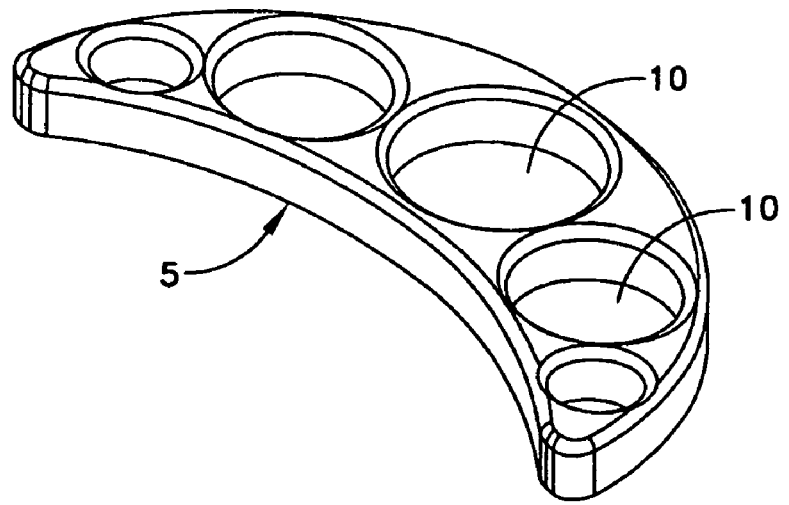
FIG. 4 is a schematic view showing an alternative form of mitral shield formed in accordance with the present invention.

A perforated shield over the affected leaflet will be sufficient to prevent leaflet prolapse while maintaining adequate blood flow. Thus, in FIG. 3, a plurality of radially elongated perforations 10 are provided in mitral shield 5. Alternatively, circular perforations, such as the circular perforations 10 provided in the mitral shield 5 shown in FIG. 4, may also be provided. Still other perforation configurations, in both shape and number, will be apparent to those skilled in the art in view of the present disclosure.

The mitral shield may be constructed of biological material (e.g., human or bovine pericardium) or non-biological material (e.g., Dacron, PTFE, a biocompatible plastic, a biocompatible metal such as titanium, nitinol wire, etc). It may also consist of autologous cells grown on a matrix or frame. The sheet may be attached to the annulus using sutures, staples, wire, medical grade adhesives or other means of fixation. Thus, for example, in FIG. 3 staples 15 are shown attaching shield 5 to the annulus of the valve.

Figure 5:
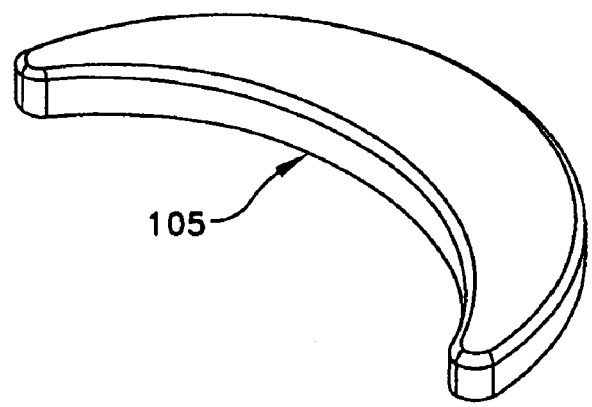
FIG. 5 is a schematic view showing another alternative form of mitral shield formed in accordance with the present invention.
Figure 6:
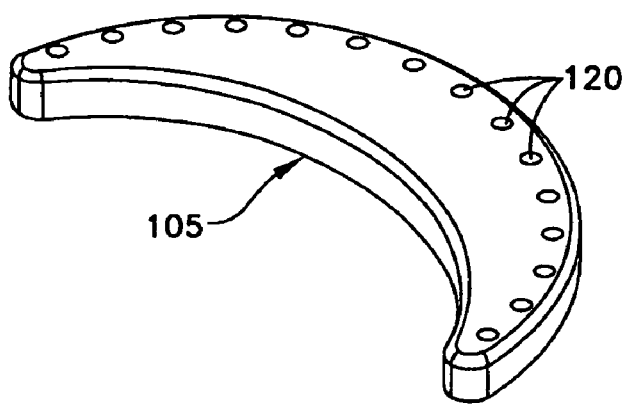
FIG. 6 is a schematic view showing still another form of mitral shield also formed in accordance with the present invention.
Figure 7:
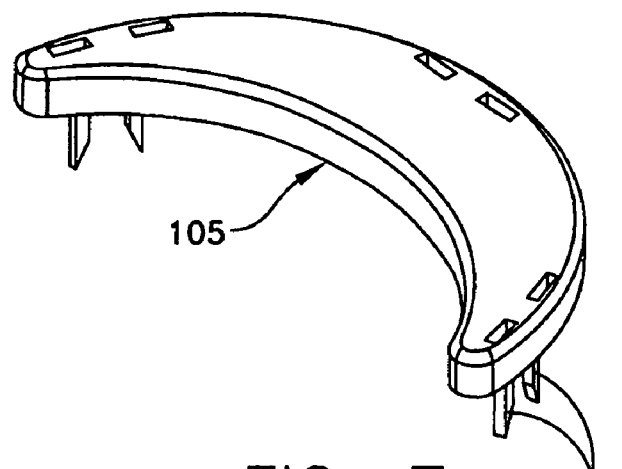
FIG. 7 is a schematic view showing yet another form of mitral shield formed in accordance with the present invention.

If the posterior annulus is dilated, a solid portion of a shield will fill the void and provide a contact surface for the anterior leaflet. Thus, for example, in FIG. 5 there is shown a mitral shield 105 which is substantially solid. In FIG. 6, there is shown a mitral shield 105 which is solid except for pre-formed suture holes 120. In FIG. 7 there is shown a mitral shield 105 which is solid and includes integral fixation staples 125.

It should be appreciated that the native posterior valve leaflet may either be excised or left in situ when the mitral shield 105 is employed.

Figure 8:
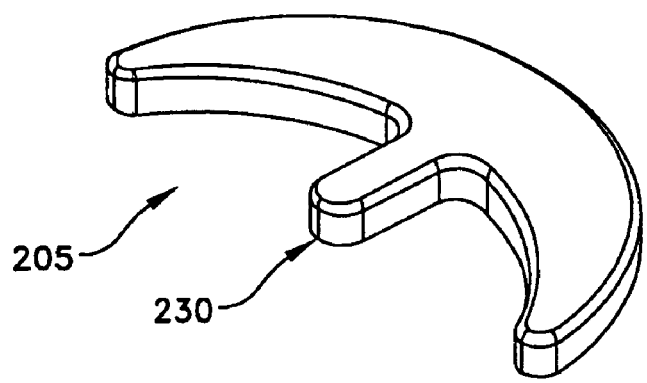
FIG. 8 is a schematic view showing another alternative form of mitral shield formed in accordance with the present invention.

Looking next at FIG. 8, there is shown a solid crescent shield 205 which is configured to correct posterior leaflet flail, and which is also provided with a mid-line projection 230 to support the anterior leaflet AL from prolapsing.

Figure 9:
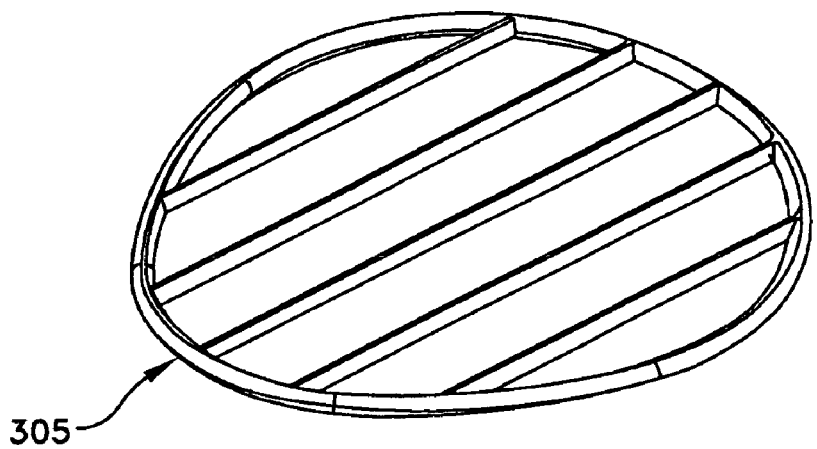
FIG. 9 is a schematic view showing still another alternative form of mitral shield formed in accordance with the present invention.

In FIG. 9, there is shown a wire frame shield 305 for addressing posterior and/or anterior leaflet prolapse only.

Figure 10:
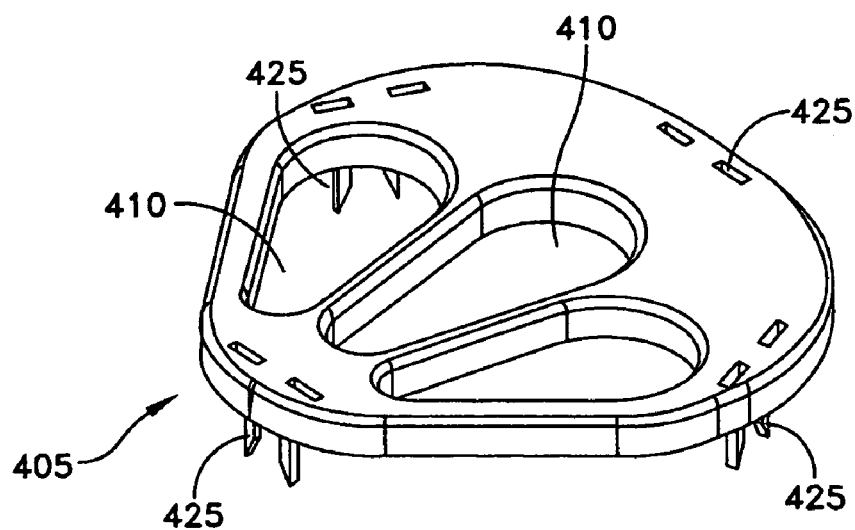
FIG. 10 is a schematic view showing yet another alternative form of mitral shield formed in accordance with the present invention.

And in FIG. 10, there is shown a mitral shield 405 combining a solid shield portion and perforations 410 and integral staples 425 around the entire annulus circumference.

Alternative designs of the same invention allow for correcting one or both leaflets while maintaining adequate blood flow. The shield may also be used in conjunction with other mitral valve repair techniques and devices.

Although the device described is intended primarily for mitral valve repair, it is also contemplated that the same or substantially similar apparatus and methodology may be used in repairing other cardiac valves, including the tricuspid, pulmonary and aortic valves.

What is claimed is:

1. A valve shield comprising a substantially flat shaped sheet of material structured for affixing to an annulus of a cardiac valve having first and second leaflets, said shaped sheet of material being of substantially uniform thickness and sized to have a surface area and a surface configuration substantially matching a substantially total surface area and a substantially total surface configuration of the first leaflet of the valve, and shaped complimentarily to the second leaflet so as to be substantially wholly contactable by an edge portion of the second leaflet of the valve, whereby to facilitate interengagement of the second leaflet edge portion and an edge portion of the sheet of material to effect closing of the valve.

2. A valve shield according to claim 1 wherein the shaped sheet of material when affixed to the cardiac valve annulus prevents prolapse of the first leaflet.

3. A valve shield according to claim 2 wherein a total surface configuration of the shaped sheet of material is substantially crescent shaped.

4. A valve shield according to claim 2 wherein a total surface area of the shaped sheet of material includes at least one opening therein.

5. A valve shield according to claim 2 wherein a total surface area of the shaped sheet of material is substantially solid.

6. A valve shield according to claim 2 wherein the shaped sheet of material is of a structure capable of being affixed to the annulus of the valve with sutures.

7. A valve shield according to claim 2 wherein the shaped sheet of material comprises non-biological material.

8. A method for reducing regurgitation in a cardiac valve having first and second leaflets and an annulus, the method comprising:
   providing a valve shield comprising a shaped sheet of material having a surface area and surface configuration substantially matching the entirety of the surface area and surface configuration of the first leaflet of the valve, and the shaped sheet of material having an edge configuration complementary to an edge configuration of the second leaflet of the valve; and
   affixing the valve shield to the annulus of the valve so that the shield substantially overlies the entirety of the first leaflet of the valve, to facilitate closing of the valve by edge to edge contact between the edge of the shaped sheet of material and the edge of the second leaflet.

9. A valve shield according to claim 1 wherein said shaped sheet of material is provided with an outer periphery at least in part shaped complimentarily to at least a portion of the annulus of the valve.

\* \* \* \* \*